(12) United States Patent
Dowling

(10) Patent No.: US 8,697,205 B2
(45) Date of Patent: Apr. 15, 2014

(54) ELASTOMERIC TUBE AND METHOD OF MAKING SAME

(75) Inventor: Kenneth Dowling, Bro (SE)

(73) Assignee: St. Jude Medical AB, Jarfalla (SE)

( * ) Notice: Subject to any disclaimer, the term of this patent is extended or adjusted under 35 U.S.C. 154(b) by 1924 days.

(21) Appl. No.: 11/913,781

(22) PCT Filed: May 17, 2005

(86) PCT No.: PCT/SE2005/000706
§ 371 (c)(1),
(2), (4) Date: Nov. 7, 2007

(87) PCT Pub. No.: WO2006/123975
PCT Pub. Date: Nov. 23, 2006

(65) Prior Publication Data
US 2008/0183262 A1 Jul. 31, 2008

(51) Int. Cl.
*B29D 23/00* (2006.01)
(52) U.S. Cl.
USPC .......................................... 428/34.1; 264/150
(58) Field of Classification Search
USPC ................ 607/20; 264/171.26, 150; 428/34.1
See application file for complete search history.

(56) References Cited

U.S. PATENT DOCUMENTS

| | | | |
|---|---|---|---|
| 4,147,832 A | 4/1979 | Namiki | |
| 5,306,568 A | 4/1994 | Matsuda et al. | |
| 5,451,206 A * | 9/1995 | Young | 604/43 |
| 5,767,183 A * | 6/1998 | Takei et al. | 524/430 |
| 6,073,657 A | 6/2000 | Hippeläinen et al. | |
| 6,136,258 A * | 10/2000 | Wang et al. | 264/514 |
| 6,516,126 B1 | 2/2003 | Rous et al. | |

FOREIGN PATENT DOCUMENTS

| | | |
|---|---|---|
| EP | 1 507 110 | 3/2007 |
| WO | WO 98/44050 | 10/1998 |

* cited by examiner

*Primary Examiner* — Christopher D Koharski
*Assistant Examiner* — Michael Carey

(57) ABSTRACT

In an elastomeric tube and a method for making such a tube, two medical-grade silicone rubber compositions are coaxially coextruded to form a tube. The compositions respectively differ in at least one physical property and respectively have similar curing conditions. The two compositions are blended at an interface formed between the two compositions during the coextruding, so that between 1-99% of the tube forms a blended gradient. The coextruded tube is then cured.

13 Claims, 1 Drawing Sheet

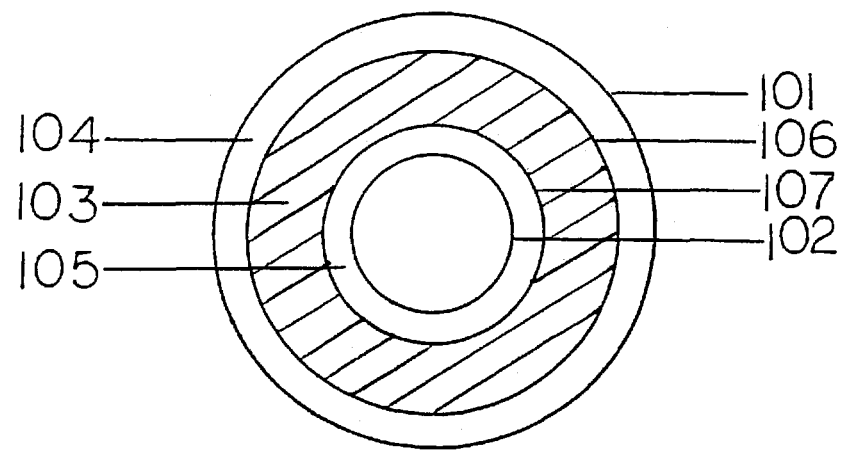

ELASTOMERIC TUBE AND METHOD OF MAKING SAME

BACKGROUND OF THE INVENTION

1. Field of the Invention

The invention relates to elastomeric tubes, more specifically, to tubes having at least two silicone rubber compositions blended at an interface to form a gradient. In particular, the invention relates to medical-grade silicone rubber tubes useful as cardiac pacemaker lead insulation.

2. Description of the Prior Art

Elastomeric tubes are used in a variety of applications and produced in numerous ways. One type of elastomeric tubes, silicone rubber tubes or lumens, are widely used in medical applications. For example, silicone rubber lumens are often used to insulate the electronic lead portion of implantable cardiac pacemakers. This is largely due to their unique combination of properties, including low toxicity, high thermal stability, good moisture resistance, excellent flexibility, high ionic purity, low alpha particle emissions, and good adhesion to various substrates.

To form silicones, one can begin with organopolysiloxane compositions which are then cured. The curing method can be, for example, through hydrosilylation where an addition reaction of silicon-bonded lower alkenyl radicals with silicon-bonded hydrogen atoms occurs. Further, curing can be catalysed with, for example, platinum. Another curing option is peroxide initiated curing, where peroxide free radicals initiate the combination of pendant vinyl groups to form cross links.

Methods and materials for preparing linear, branched, and cyclic organopolysiloxanes and other starting materials are well known in the art, as are various curing methods. The goal of the curing is to form some sort of cross-link or junction between and among the polymer strands to create a continuous network or gel.

Presently, silicone rubber lumens are selected for use based on a particular desired property. One type of silicone may be useful where tear resistance is desired; another useful where crush resistance is necessary. In some cases, dual- or multi-layer silicone rubber lumens have been produced in an attempt to maximize desirable properties and/or to provide differing properties at different surfaces of the lumen.

There are inherent drawbacks with present silicone rubber lumens. Single-layer lumens may not possess all desired properties, whereas dual-layer lumens often have problems with delamination at the interface of the two silicones, particularly when subjected to shear forces. Further, as emerging applications for silicone lumens grow, the specific demands of new products require new and improved lumens. There is a need to meet these challenges.

SUMMARY OF THE INVENTION

An object of the present invention is to resolve problems faced by both single and multi-layer lumens by providing an elastomeric tube of the type having at least two compositions blended together at their interface to form a gradient of properties and compositions dispersed therethrough.

The above object is achieved in accordance with the invention by a method for making an elastomeric tube including coaxially coextruding at least two medical-grade silicone rubber compositions to form a tube, blending the two compositions at an interface formed between the compositions during coextruding so that between 1-99% of the tube forms a blended gradient, and curing the coextruded tube, wherein the compositions differ in at least one physical property and the compositions have similar curing conditions. The curing step can be, for example, curing with platinum or by peroxide cross-linking. At least 1% of the tube can comprise the blended gradient, preferably at least 5%, more preferably at least 25%.

According to a further embodiment of the invention, a method of making an insulated cardiac lead is provided, including providing a tube according to the first embodiment then inserting an electrode into the tube.

The above object also is achieved by an apparatus for making an elastomeric tube is provided that includes an extruder for coaxially coextruding at least two medical-grade silicone rubber compositions, a blender for simultaneously blending between 1% and 99% of the compositions at an interface formed between the compositions during coextrusion, and a curing unit for curing the coextruded tube, wherein the compositions differ in at least one physical property and the compositions have similar curing conditions. The curing unit can, for example, implement the curing with platinum or by peroxide cross-linking. The blender can include a control unit for manipulating feed rates of the two compositions.

According to a further embodiment of the invention, a silicone rubber tube is provided that has a hollow elongated body extending between a distal end and a proximal end and having an outer surface formed of a first medical grade silicone rubber composition, an inner surface formed of a second medical grade silicone rubber composition coaxial thereto and forming a longitudinally extending opening therethrough, and a graduated mixture of the first and second composition therebetween, wherein the first and second compositions differ in at least one physical property and have similar curing conditions.

The first composition may have at least one property selected from the group consisting of a tear strength in the range of 30-60 N/mm and a tensile strength of 8-15 MPa. The second composition may have at least one property selected from the group consisting of at least tensile strength of at least 7 MPa and an abrasion resistance according to the Taber Abrasion test (ASTM D4060) of less than 500 mg at 3000 cycles with 1000-g load and H-18 (fine) wheels. The graduated mixture may have at least one property selected from the group consisting of a tear strength of at least 35 M/mm and a tensile strength of at least 8.5 MPa. The tube may further have a polyvinyl tube coaxial and adjacent to the outer surface. The tube may further comprise a cardiac lead extending between the distal and proximal ends. The tube may have an outer diameter in the range of 3-34 French and/or an inner diameter in the range of 3-34 French. An implantable medical catheter according to the invention may include such a tube.

For convenience, certain terms employed in the specification, examples, and appended claims are collected here.

As used herein, the term "silicone" refers to any of the class of polymers of $R_2SiO$ where R is a hydrocarbon. Different silicones have different mechanical properties. Certain of these properties such as tear strength, abrasion resistance, resistance to shredding, compression set, crush and creep resistance are of particular importance in the materials and methods described herein.

The term "medical grade" refers to materials which are of particular character and sufficient quality to be used in products or devices that will come in contact with a patient, with a patient's bodily fluids or parts, or with materials or medicaments which will be used in conjunction with treating a patient.

The terms "curing" and "curing conditions" relate to the treatment or process by which starting materials are crosslinked or otherwise formed into a network. It may be possible for materials to self-cure, that is, that no additional treatment or materials are required. Examples of known curing methods include platinum-catalyzed hydrosilylation of organopolysiloxane compositions into silicone and free radical initiated vinyl-vinyl binding.

"Gradient" is used to mean a gradual degree of change formed by mixing at least two compositions. In such a mixture, the outermost portion of each composition remains pure, the inner portion comprises a gradual change from 99% pure to 1% pure, with the percentage of the second layer component comprising the remaining percentage of the mixture in the case of two components.

For convenience, the description herein largely relates to an elastomeric tube or lumen configured as an insulator for a cardiac pacemaker lead. The present invention, however, relates to all configurations and uses. Other medical uses include but are not limited to electronic implant devices such as those monitoring glucose levels or stimulating muscle function. Further industrial uses for tubing such as that provided by the present invention are known in the art.

The present invention contemplates the addition of a variety of compounds, coatings or treatments such as polyvinyl pyrrolidone outer layers, surface treatment with a plasma generator, and coating with anti-clotting agents. The present invention is compatible with these existing materials and processes, and is expected to be compatible with modifications and new materials and methods developed in the future.

BRIEF DESCRIPTION OF THE DRAWINGS

The FIGURE shows a cross-sectional view of an elastomeric tube according to the present invention.

DESCRIPTION OF THE PREFERRED EMBODIMENTS

While the present invention will be described with specificity in accordance with certain of its preferred embodiments, the following examples serve only to illustrate the invention and are not intended to limit the same. If sources are not specifically described, materials and methods are known and commercially available.

As shown in the FIGURE, an elastomeric tube 100 according to the present invention comprises an outer surface 101 and an inner surface 102. Between surfaces 101, 102, lies a region of gradient 103. The extent of the region of the gradient 103 can encompass nearly all of tube 100, only a small portion of tube 100, or something in between.

The tube depicted in the FIGURE is formed using two compositions. The first composition 104 lies on the outer portion of tube 100, and the second composition 105 lies on the inner portion of tube 100. At least some portion of tube 100 comprises pure first composition 104 and at least some portion comprises pure second composition 105. The remainder of tube 100 comprises region of gradient 103. This region may be centered, as shown in the FIGURE.

Region of gradient 103 has an outer border 106 and an inner border 107. Although borders 106, 107 are represented by solid lines in the FIGURE, borders 106, 107 are not necessarily precise and involve an interblending of the two or more compositions. At outer border 106, region of gradient 103 is primarily comprised of first composition 104. At inner border 107, region of gradient 103 is primarily comprised of second composition 105. By blending compositions 104, 105 as they are extruded, a mixture comprising the two is formed. It is believed that the polymers form covalent bonds prior to curing, providing a bonded, cured blend.

Theoretically, the mixture will go from 99% of the first composition at a region adjacent to the pure first composition area to 1% of the first composition at a region adjacent to the pure second composition area. Depending on the desired outcome, this mixture can be a steep or sloped gradient, and can allow for a very large relative area comprised of the respective pure compositions or only a single molecular layer.

In applications where more than two silicones are used, it can be desired to have distinct layers of each or only distinct layers of those silicones forming the outer and inner layers. For example, in a three-silicone lumen, the first silicone can comprise the outer layer and a portion of the blended region. The second silicone can form a mixture with the first in the blended region, have a pure layer opposite to the outer layer, and form a mixture with a third polymer, the third polymer also forming the inner layer. Alternatively, the outer and inner layers can be distinct, pure polymer, whereas the central portion of the tube can comprise a blended gradient consisting of the polymers of the outer and inner layers, respectively, as well as a third polymer.

For testing purposes and to refine production methods, different color dyes or pigments can be added to each respective polymer prior to extrusion. After curing, the tube can be sliced into cross sections and examined to evaluate the region and gradient of blending.

The main benefit achieved by providing the gradient is that the overall desired properties of the tube or lumen can be maximized, while allowing for distinct, differing properties at each of the inner and outer surfaces. For example, certain applications call for abrasion resistance on an outer surface. This property may not be necessary on an inner surface, instead, perhaps, tear strength may be the most desirable property on the inner surface. The lumen taken as a whole may have crush resistance as the most important property. With this as a goal, present methods for single layer lumens would be limited to selecting the absolute most important of these properties and providing that throughout, or attempting to find one material which has some aspects of all three. Alternatively, one could attempt to prepare a multi-layer lumen, although such products tend to perform poorly in certain applications where the tube is subjected to longitudinal forces.

Without wanting to be bound by theory, it is understood that multi-layer lumens only have minimal cross-linking at the interface, which linking can be disrupted by outside forces. According to the present invention, mixing offers the additional benefit of blending the polymers throughout the mixed region, followed by cross-linking then curing, forming a more stable product.

With the inventive method, a lumen can be provided where the composition forming the outer surface has good abrasion resistance, the composition forming the inner surface has good tear resistance, the blended gradient has good crush resistance, and the lumen performs well as a whole. Due to the gradient and the interblending of the compositions, the problems of delamination are avoided while still providing an array of configurations to suit the application at hand.

In addition to maximizing desired properties and avoiding delamination, the present invention provides lumens which may be smaller than conventional multi-layer lumens. Any size reduction achieved by the blended gradient can be favorable, particularly with cardiac pacemaker lead insulators. In addition to minimizing patient discomfort it can reduce the noticeable protrusions along the implant path, among other benefits.

The mixing of the compositions concurrently with extrusion can be achieved by any method known or developed in the art. Examples include selecting for extrusion dies that will provide compositions formed with corresponding indentations and protrusions so that together they form an interlocking surface at their points of contact. Alternatively, feed rates for the different compositions could be varied and/or the dies could be concentrically rotated, causing surface tension and mixing.

The curing of the compositions can comprise any known or developed method. Since the mixed, extruded tube will be cured as a unit, it is necessary that the compositions used in the tube cure using the same chemical mechanism.

While the FIGURE shows tube 100 with smooth outer and inner surfaces 101, 102, these can be shaped as desired. For example, the inner surface could be formed with an extrusion die having inwardly directed projections, making a number of parallel longitudinally extending grooves which can help reduce the coefficient of friction. Further, surfaces of the tube may be treated or coated or otherwise provided with additional members as known in the art.

Example 1

Cardiac Pacemaker Lead Insulator

A lumen can be formed having properties maximized for use as an insulator for a cardiac pacemaker lead. Such a lumen would ideally be strong, flexible, and tear resistant throughout, particularly abrasion resistant, tear resistant, and having a surface which is easy to bind to on the outside, while having reduced friction, maximum pull strength, crush fatigue resistance and cold flow resistance on the inside.

The method of the present invention allows for such maximization of desired surface properties and desired bulk properties. Two compositions can be selected which meet the respective goals of the inner and outer surfaces. The best gradient for maximizing bulk properties can be selected using theoretical estimates or by testing different tube sections. It may be that having a nearly 50:50 mix throughout, excepting the edges, is desired. Alternatively, it may be that a gradual change having 1:99 at the inner edge of the gradient area to 99:1 at the outer edge of the gradient area is preferred. Further, the thickness of the unmixed compositions, that is, pure first and second compositions, may be equivalent or different.

In an exemplary tube, a layer of Dow Corning silicone (Q7-4780, 0.16 mm wall thickness, Dow Corning, Inc.) and a layer of NuSil Med-4770 silicone (Med-4770, 0.16 mm wall thickness, NuSil Technologies, Inc.) can be mixed in a coextrusion die and cured by a platinum-catalyzed addition reaction initiated by heat. The resulting tube would have the desired properties of resistance to abrasion by hard surfaces on the outside, high tear strength inside, and an overall high tensile strength in the bulk of the article. The mixing could be manipulated to provide a 0.1 mm Med-4770 layer outside, a 0.12 mm gradient from Med-4770 to Q7-4780, and a 0.1 mm Q7-4780 layer inside.

Cardiac lead insulators produced by this method may have inner diameters in the range of 0.4 to 5.0 mm and outer diameters in the range of 0.6 to 8.0 mm.

Example 2

Implanted Glucose Monitor

In a developing area of medicine, electronic monitors which continually contact and monitor glucose levels in blood are being refined. These typically comprise flexible sensors, often thin film sensors having a plurality of conductive elements encased between insulating layers. Exposed electrodes contact a patient's blood or other body fluid when the sensors are placed subcutaneously. Emerging from the patient is a set of corresponding conductive contacts which connect to an externally-located monitoring device. Devices may eventually be located entirely internal in a patient, and may further comprise insulin- or other drug-delivery systems or infusion pumps operating in cooperation therewith.

At the present, the implanted sensor portion must contact bodily fluids at only at the terminal end of the sensor, the rest of the implant must be isolated from fluids. Tubes for the protected portion are therefore required. Such tubes could be used as coatings for entire devices if they are totally implantable.

Ideal properties of a lumen used as an insulator for glucose monitoring sensors would take into account factors such as the chosen location and depth of placement as well as the number and type of elements encased therein.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

I claim as my invention:

1. A method for making an elastomeric tube, comprising:
   coaxially coextruding at least two medical-grade silicone rubber compositions, respectively differing in at least one physical property and respectively having similar curing conditions, to form a tube;
   blending the two compositions at an interface formed between the at least two compositions during the coextruding so that between 1-99% of the tube forms a blended gradient of the two compositions with respect to a cross-section of the tube; and
   curing the coextruded tube.

2. A method according to clam 1, comprising curing the extruded tube with platinum.

3. A method according to claim 1, comprising curing the extruded tube by peroxide cross-linking.

4. A method according to claim 1, comprising blending the at least 1% of the tube comprises the blended gradient.

5. A method according to claim 1, comprising inserting an electrode into the tube.

6. A silicone rubber tube, comprising:
   a hollow elongated body extending between a distal end and a proximal end and having an outer surface;
   an inner surface coaxial thereto and forming a longitudinally extending opening therethrough;
   a first medical grade silicone rubber composition comprising the outer surface;
   a second medical grade silicone rubber composition comprising the inner surface; and
   a graduated mixture of the first composition and the second composition therebetween;
   wherein the first composition and the second composition differ in at least one physical property; and
   wherein the first composition and the second composition have similar curing conditions.

7. A tube according to claim 6, wherein the first composition has at least one property selected from the group consisting of a tear strength in the range of 30-60 N/mm and a tensile strength of 8-15 MPa.

8. A tube according to claim 6, wherein the second composition has at least one property selected from the group consisting of a tensile strength of at least 7 MPa and an abrasion resistance according to the Taber Abrasion test (ASTM D4060) of less than 500 mg at 3000 cycles with 1000-g load and H-18 (fine).

9. A tube according to claim 6, wherein the graduated mixture has at least one property selected from the group consisting of a tear strength of at least 35 M/mm and a tensile strength of at least 8.5 MPa.

10. A tube according to claim 6, further comprising a polyvinyl tube coaxial and adjacent to the outer surface.

11. A tube according to claim 6, further comprising a cardiac lead extending between the distal end and the proximal end.

12. A tube according to claim 6, wherein the tube has an outer diameter in the range of 3-34 French.

13. A tube according to claim 6, wherein the tube has an inner diameter in the range of 3-34 French.

* * * * *